United States Patent
Liu et al.

(10) Patent No.: US 10,401,462 B2
(45) Date of Patent: Sep. 3, 2019

(54) SYSTEM AND METHOD FOR CALIBRATING GRADIENT DELAY IN MAGNETIC RESONANCE IMAGING

(71) Applicant: UIH AMERICA, INC., Houston, TX (US)

(72) Inventors: Qi Liu, Houston, TX (US); Yu Ding, Houston, TX (US)

(73) Assignee: UIH AMERICA, INC., Houston, TX (US)

(*) Notice: Subject to any disclaimer, the term of this patent is extended or adjusted under 35 U.S.C. 154(b) by 190 days.

(21) Appl. No.: 15/394,974

(22) Filed: Dec. 30, 2016

(65) Prior Publication Data
US 2018/0188343 A1 Jul. 5, 2018

(51) Int. Cl.
*G01R 33/565* (2006.01)
*A61B 5/055* (2006.01)
*G01R 33/48* (2006.01)

(52) U.S. Cl.
CPC ........ *G01R 33/56572* (2013.01); *A61B 5/055* (2013.01); *G01R 33/56518* (2013.01); *G01R 33/4824* (2013.01)

(58) Field of Classification Search
CPC ........ G01R 33/56572; G01R 33/56518; G01R 33/4824
See application file for complete search history.

(56) References Cited

U.S. PATENT DOCUMENTS

| | | | | |
|---|---|---|---|---|
| 6,188,219 B1* | 2/2001 | Reeder | ............... | G01R 33/58 324/307 |
| 2013/0271137 A1* | 10/2013 | Griswold | ........... | G01R 33/5611 324/314 |
| 2014/0005969 A1* | 1/2014 | Weng | ................ | G01R 35/005 702/104 |
| 2014/0375316 A1 | 12/2014 | Fenchel et al. | | |
| 2017/0356972 A1* | 12/2017 | Wheaton | ............ | G01R 33/3854 |

OTHER PUBLICATIONS

Fast, Simple Gradient Delay Estimation for Spiral MRI, Ryan K. Robison, Ajit Devaraj and James G. Pipe, Magnetic Resonance in Medicine, 63:1683-1690 (2010) (Year: 2010).*

(Continued)

*Primary Examiner* — G. M. A Hyder
(74) *Attorney, Agent, or Firm* — Metis IP LLC

(57) ABSTRACT

A system and method for magnetic resonance imaging is provided. The method includes acquiring a first set of MR signals and a second set of MR signals by applying a pulse sequence on a subject. The method also includes obtaining a first data line by filling the first set of MR signals into k-space along a first trajectory, and obtaining a second data line by filling the second set of MR signals into k-space along a second trajectory. The method also includes determining a candidate k-space shift based on the first data line and the second data line, and determining a candidate gradient delay based on the candidate k-space shift obtained in each of a plurality of iterations. The method also includes reconstructing an image of the subject based on the candidate gradient delay obtained in the last iteration.

20 Claims, 11 Drawing Sheets

(56) References Cited

OTHER PUBLICATIONS

Payal Bhaysar, "Fast Variable System Delay Correction for Spirla MRI", Thesis, Master of Science, Arizona State University, Dec. 2013. (Year: 2013).*
Niklas Huebel et al., "Anions Govern Cell Volume: A Case Study of Relative Astrocytic and Neuronal Swelling in Spreading Depolarization", Plos One, DOI: 10.1371, Mar. 14, 2016.
David K. Hammond et al., "Cortical graph smoothing : a novel method for exploiting DWI-derived anatomical brain connectivity to improve EEG source estimation", IEEE Trans Med Imaging, 32(10): 1952-1963, Oct. 2013.
Thiele Kobus et al., "Metabolite Ratios in H MR Spectroscopic Imaging of the Prostate", Magnetic Resonance in Medicine,73: 1-12(2015).
Jeff H. Duyn et al., "Simple Correction Method for k-Space Trajectory Deviations in MRI", Journal of Magnetic Resonance .132: 150-153(1998).
Herrmann K-H, Krämer M, Reichenbach JR (2016) Time Efficient 3D Radial UTE Sampling with Fully Automatic Delay Compensation on a Clinical 3T MR Scanner. PLoS One 11(3): e0150371.
Yuli Huang, Ultrashort Echo-Time MR Imaging at Low Field, 2015.

* cited by examiner

SYSTEM AND METHOD FOR CALIBRATING GRADIENT DELAY IN MAGNETIC RESONANCE IMAGING

TECHNICAL FIELD

The present disclosure generally relates to magnetic resonance imaging (MRI), and more particularly, to a system and method for data processing in MRI.

BACKGROUND

Magnetic resonance imaging (MRI) is a noninvasive medical technique, which is widely used to generate images of a region of interest (ROI) by exploiting a powerful magnetic field and radio frequency (RF) techniques. During an MRI process, a set of acquired signals may be processed and filled into a k-space, and then data in the k-space may be subjected to Fourier transformation to reconstruct MRI images. MRI images may suffer from ghost artifacts. To obtain images with low ghost levels, it is important to control signal stability and timing. Unfortunately, MRI system may suffer from gradient delay, eddy currents, or imperfections in gradient amplifier. These factors may cause k-space trajectory deviation from design and, thus, increase ghost levels of the MRI images. Therefore, it is desirable to reduce ghost levels of the MRI images effectively and to make the image clearer.

SUMMARY

In a first aspect of the present disclosure, a method for magnetic resonance imaging is provided. The method may include one or more of the following operations. A first set of MR signals and a second set of MR signals may be acquired by applying a pulse sequence on a subject, the pulse sequence including at least an imaging pulse and a pre-scan pulse. A first data line may be obtained by filling the first set of MR signals into k-space along a first trajectory. A second data line may be obtained by filling the second set of MR signals into k-space along a second trajectory. A candidate k-space shift may be determined based on the first data line and the second data line. A plurality of iterations may be performed. During each of the iterations, a candidate gradient delay may be determined based on the candidate k-space shift obtained from a prior iteration; the first data line and the second data line may be updated based on the candidate gradient delay; and the candidate k-space shift may be updated based on the updated first data line and the updated second data line. The candidate gradient delay obtained in the last iteration may be determined as the gradient delay. An image of the subject may be reconstructed based on the gradient delay.

In a second aspect of the present disclosure, a system for magnetic resonance imaging is provided is provided. The system may include an MRI scanner and a processing module. The MRI scanner may be configured to acquire a first set of MR signals and a second set of MR signals by applying a pulse sequence on a subject, the pulse sequence including at least an imaging pulse and a pre-scan pulse. The processing module may be configured to perform one or more of the following operations. A first data line may be obtained by filling the first set of MR signals into k-space along a first trajectory. A second data line may be obtained by filling the second set of MR signals into k-space along a second trajectory. A candidate k-space shift may be determined based on the first data line and the second data line. A plurality of iterations may be performed. During each of the iterations, a candidate gradient delay may be determined based on the candidate k-space shift obtained from a prior iteration; the first data line and the second data line may be updated based on the candidate gradient delay; and the candidate k-space shift may be updated based on the updated first data line and the updated second data line. The candidate gradient delay obtained in the last iteration may be determined as the gradient delay. An image of the subject may be reconstructed based on the gradient delay.

In a third aspect of the present disclosure, a non-transitory computer readable medium is provided. The non-transitory computer readable medium storing instructions, the instructions, when executed by a computer, may cause the computer to implement a method. The method may include one or more of the following operations. A first set of MR signals and a second set of MR signals may be acquired by applying a pulse sequence on a subject, the pulse sequence including at least an imaging pulse and a pre-scan pulse. A first data line may be obtained by filling the first set of MR signals into k-space along a first trajectory. A second data line may be obtained by filling the second set of MR signals into k-space along a second trajectory. A candidate k-space shift may be determined based on the first data line and the second data line. A plurality of iterations may be performed. During each of the iterations, a candidate gradient delay may be determined based on the candidate k-space shift obtained from a prior iteration; the first data line and the second data line may be updated based on the candidate gradient delay; and the candidate k-space shift may be updated based on the updated first data line and the updated second data line. The candidate gradient delay obtained in the last iteration may be determined as the gradient delay. An image of the subject may be reconstructed based on the gradient delay.

In a fourth aspect of the present disclosure, a method for determining a gradient delay in a magnetic resonance system is provided. The method may include one or more of the following operations. A first set of MR signals and a second set of MR signals may be acquired by applying a pulse sequence on a subject, the pulse sequence including at least an imaging pulse and a pre-scan pulse. A first data line may be obtained by filling the first set of MR signals into k-space along a first trajectory. A second data line may be obtained by filling the second set of MR signals into k-space along a second trajectory. The gradient delay may be iteratively determined based on a k-space shift in response to the first data line and the second data line determined based on the iterative process including iteratively updating the first data line and the second data line after each iteration of the iterative process based on an updated gradient delay determined by the most recent iteration of the iterative process.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Figure 1A:
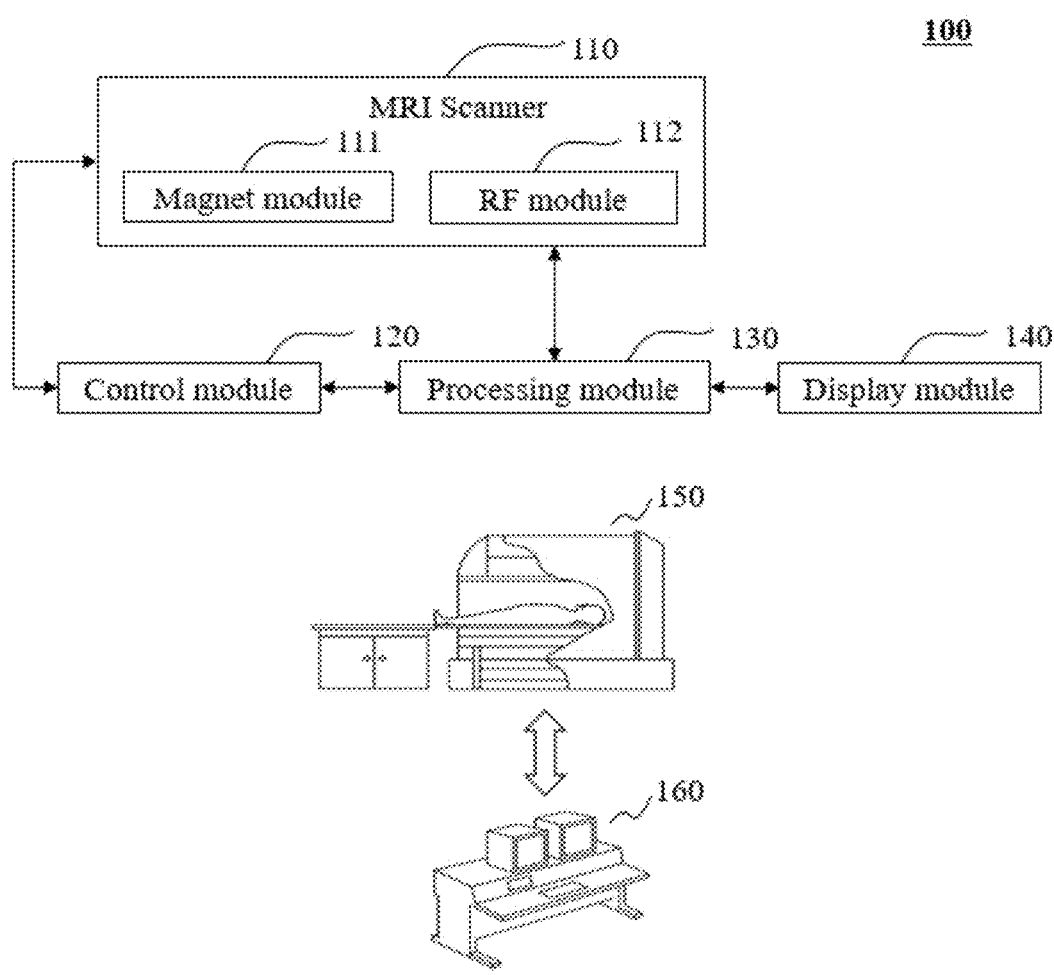
FIG. 1A is a block diagram of a magnetic resonance imaging (MRI) system according to some embodiments of the present disclosure.

FIG. 1A is a block diagram of a magnetic resonance imaging (MRI) system according to some embodiments of the present disclosure. As illustrated, the MRI system 100 may include an MRI Scanner 110, a control module 120, a processing module 130, and a display module 140. The MRI Scanner 110 may include a magnet module 111 and a radio frequency (RF) module 112. In some embodiments, the MRI Scanner 110 may perform a scan on a subject. In some embodiments, the scan may be an imaging scan for generating a magnetic resonance (MR) image, or a pre-scan for calibrating the MRI system 100. The magnet module 111 may include a main magnet field generator and/or a gradient magnet field generator (not shown in FIG. 1). The main magnet field generator may create a static magnetic field $B_0$ during a scan. The main magnet field generator may be of various types including, for example, a permanent magnet, a superconducting electromagnet, a resistive electromagnet, etc. The gradient magnet field generator may generate magnet field gradients Gx, Gy, Gz in the "X", "Y", "Z" directions, respectively. As used herein, the X, Y and Z direction may represent X, Y and Z axis in a coordinate system. Merely by way of example, the X axis and the Z axis may be in a horizontal plane, the X axis and the Y axis may be in a vertical plane, the Z axis may be along the rotational axis of the gantry. In some embodiments, the X axis, the Y axis, and the Z axis may be specified by the gradient magnet field generator (i.e., gradient coils in the gradient magnet field generator). The gradient magnet field may encode and/or readout the spatial information of the subject located within the MRI Scanner 110. In some embodiments, the magnet module 111 may generate magnet field gradients in a set of directions during a scan. In some embodiments, the scan may be a quick calibration pre-scan to calibrate a gradient delay resulted from a time delay when switching on/off the gradient magnet field generator. The magnet field gradients in the pre-scan may include an additional dephaser gradient to calibrate the gradient delay. The details of the dephaser gradient may be disclosed in other parts of the present application, for example in FIG. 6A and/or FIG. 6B, and the description thereof. Merely by way of example, the magnet module 111 may generate a first magnet field gradient in a first direction, a second magnet field gradient in a second direction, and a third magnet field gradient in a third direction. In some embodiments, the first, second, and third direction, may be along the X axis, the Y axis, and the Z axis, respectively. In some embodiments, the magnet field gradients along the X axis, the Y axis, and/or the Z axis may correspond to different encoding/readout directions in the k-space (e.g., the direction of the $k_x$ axis, the direction of the $k_y$ axis, the direction of the $k_z$ axis, or any other direction). The RF module 112 may include RF transmitting coils and/or receiving coils. These RF coils may transmit RF signals to, or receive RF signals from a subject of interest. In some embodiments, the function, size, type, geometry, position, amount, and/or magnitude of the magnet module 111 and/or of the RF module 112 may be determined or changed according to one or more specific conditions. For example, according to the difference in function and/or size, the RF coils may be classified as volume coils and local coils. In some embodiments, the volume coils may include birdcage coils, transverse electromagnetic coils, surface coils, saddle coils, etc. In some embodiments of the present disclosure, the local coils may include birdcage coils, solenoid coils, saddle coils, flexible coils, etc. In some embodiments, the magnet module 111 and the radio frequency (RF) module 112 may be designed to surround a subject to form a tunnel type MRI Scanner 150 (i.e. a close-bore MRI Scanner), or an open MRI Scanner 110 (i.e. an open-bore MRI Scanner).

The control module 120 may control the magnet module 111 and/or the RF module 112 of the MRI Scanner 110, the processing module 130, and/or the display module 140. Merely by way of example, the control module 120 may control the magnet field gradients in the X direction, the Y direction, and the Z direction. In some embodiments, the control module 120 may receive information from, or send information to the MRI Scanner 110, the processing 130, and/or the display module 140. According to some embodiments, the control module 120 may receive commands from the display module 140 provided by, e.g., a user, and adjust the magnet module 111 and/or RF module 112 to take images of a subject of interest according to the received commands. Merely by way of example, the command may relate to the polarity, waveform, strength and/or timing of the magnet field gradient (e.g., the dephaser gradient).

The processing module 130 may process different kinds of information received from different modules. For further understanding the present disclosure, several examples are given below, but the examples do not limit the scope of the present disclosure. For example, in some embodiments, the processing module 130 may process MR signals received from the RF module 112 and generate one or more MR images based on these signals and deliver the images to the display module 140. In some embodiments, the processing module 130 may process data input by a user or an operator via the display module 140 and transform the data into specific commands, and supply the commands to the control module 120.

The display module 140 may receive input and/or display output information. The input and/or output information may include programs, software, algorithms, data, text, number, images, voice, or the like, or any combination thereof. For example, a user or an operator may input some initial MR parameters or conditions to initiate a scan. As another example, some information may be imported from an external resource, such as a floppy disk, a hard disk, a wireless terminal, or the like, or any combination thereof. In some embodiments, the control module 120, the processing module 130, and/or the display module 140 may be integrated into an image generator 160. A user may set parameters in an MR scan, control the imaging procedure, view the images produced through the image generator 160.

It should be noted that the above description of the MRI system 100 is merely provided for the purposes of illustration, and not intended to limit the scope of the present disclosure. For persons having ordinary skills in the art, multiple variations and modifications may be made under the teachings of the present disclosure. For example, the assembly and/or function of the MRI system 100 may be varied or changed according to specific implementation scenarios. Merely by way of example, some other components may be added into the MRI system 100, such as a patient positioning module, a gradient amplifier module, and other devices or modules. Note that the MRI system 100 may be a traditional or a single-modality medical system, or a multi-modality system including, e.g., a positron emission tomography-magnetic resonance imaging (PET-MRI) system, a remote medical MRI system, and others, etc. However, those variations and modifications do not depart from the scope of the present disclosure.

Figure 1B:
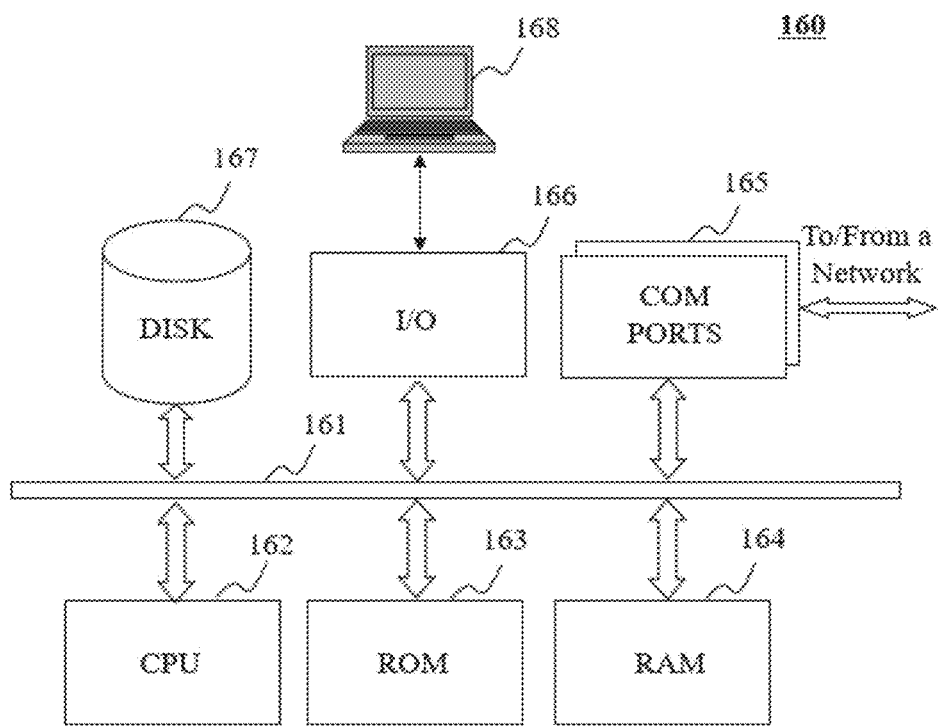
FIG. 1B illustrates an exemplary architecture of an image generator according to some embodiments of the present disclosure.

FIG. 1B illustrates an exemplary architecture of an image generator according to some embodiments of the present disclosure. In some embodiments, the control module 120, the processing module 130, and/or the display module 140, or a portion thereof, or a combination thereof, may be implemented on the image generator 160 via its hardware, software program, firmware, or a combination thereof.

The image generator 160 may include an internal communication bus 161, a central processing unit (CPU) 162, an I/O interface 166, a COM ports 165, and one or more memory devices. The internal communication bus 161 may transmit data between the components (162 through 167) of the image generator 160. For example, the MRI data from the disk 167 may be transmitted through internal communication bus 161 to the CUP 162 to generate an image.

The central processing unit (CPU) 162 may execute computer instructions. The computer instructions may relate to routines, programs, objects, components, data structures, procedures, modules, etc. In some embodiments, the CPU 162 may process the data or information received from the MRI scanner 110, the control module 120, or any other component of the MRI system 100. In some embodiments, CPU 162 may include one or more processors. The processors may include a microcontroller, a microprocessor, a reduced instruction set computer (MSC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof. For example, the processors may include a microcontroller to process the MRI data received from the MRI scanner 110 for image reconstruction.

The one or more memory devices may store the data or information received from the MRI scanner 110. In some embodiments, the memory devices may include a disk 167, a random access memory 164 (RAM), a read-only memory 163 (ROM), or the like, or any combination thereof. The disk 167 may be implemented by, for example, a magnetic disk, an optical disk, a floppy disk, an optical disk, or a zip disk, etc. The RAM 164 may be implemented by, for example, a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM 163 may be implemented by, for example, a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the memory devices may store one or more programs and/or instructions to perform exemplary methods described in the present disclosure. For example, the ROM 163 may store a program or an algorithm for reconstructing an MR image based on the MR data.

The image generator 160 may include one or more COM ports 165 connected to a network to furnish data communications. The communication ports (COM ports) 165 may transmit information to or receive information from MRI scanner 110 via a network. In some embodiments, communication ports 165 may include a wired port (e.g., a Universal Serial Bus (USB), a High Definition Multimedia Interface (HDMI), a wireless port (such as a Bluetooth port, an infrared interface, and a WiFi port), or the like, or any combination thereof.

The I/O interface 166 may support information input or output between the image generator 160 and one or more peripherals. In some embodiments, the peripherals may include a terminal, a keyboard, a touch screen, a cursor control device, a remote controller, or the like, or any combination thereof. The terminal may include, for example, a mobile device (e.g., a smart phone, a smart watch, a laptop computer, or the like), a personal computer, or the like, or any combination thereof. For example, the terminal may be implemented by a computer 168, which may be a general purpose computer or a specially designed computer. The cursor control device may include a mouse, a trackball, or cursor direction keys to communicate direction information and command selections to, for example, the processing module 130 or control cursor movement on a display device.

The information input and/or output via I/O interface 166 may include programs, software, algorithms, data, text, number, images, voices, or the like, or any combination thereof. For example, a user may input some initial parameters or conditions to initiate an MRI data processing. In some embodiments, the information input via I/O interface 166 may be input via a keyboard, a touch screen, a voice sensor, a motion sensor, a brain monitoring system, or any other devices. The information output via I/O interface 166 may be may be transmitted to the display module 140, a loud speaker, a printer, a computing device, or the like, or a combination thereof.

Those skilled in the art will recognize that the present teachings are amenable to a variety of modifications and/or enhancements. For example, although the implementation of various components described herein may be embodied in a hardware device, it may also be implemented as a software only solution, e.g., an installation on an existing server. In addition, the image processing device as disclosed herein may be implemented as a firmware, firmware/software combination, firmware/hardware combination, or a hardware/firmware/software combination.

Figure 2:
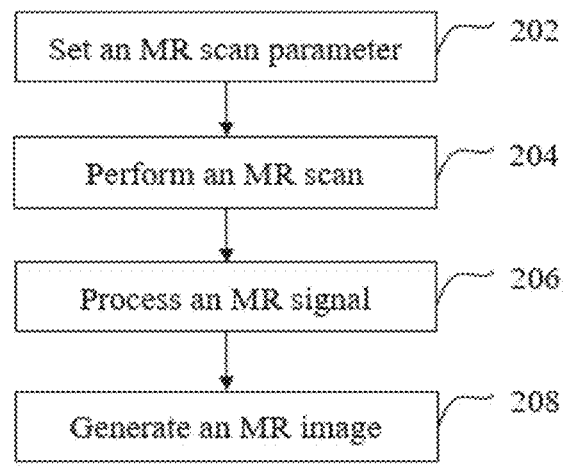
FIG. 2 is a flowchart of an MR scan according to some embodiments of the present disclosure.

FIG. 2 is a flowchart of an MR scan according to some embodiments of the present disclosure. In 202, an MR parameter may be set. The MR parameter may relate to an MR scanning, a protocol selection, a signal acquisition, a data processing, a data storage, a data calibration, an image generation, or the like, or any combination thereof. Merely by way of example, the MR parameter may include an image contrast and/or ratio, a region of interest (ROI), slice thickness, an imaging type (e.g., T1 weighted imaging, T2 weighted imaging, proton density weighted imaging, etc.), a spin echo type (spin echo, fast spin echo (FSE), fast recovery FSE, single shot FSE, gradient recalled echo, fast imaging with stead-state procession, and etc.), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. In some embodiments, the MR parameter may be set in the control module 120. In some embodiments, the MR parameter may be set via the image generator 160 through a user interface.

In 204, an MR scan may be performed by, for example, the MRI Scanner 110. In some embodiments, the MR scan may be an imaging scan for generating an image, or a pre-scan for calibrating the MRI system 100. In some embodiments, an MR parameter including a pulse sequence may be sent to the MRI Scanner 110 to generate RF excitation pulses and magnetic field gradients during the MR scan. The pulse sequence may be, for example, a spin echo (SE) sequence, a fast spin echo (FSE) sequence, an ultra-short echo-time (UTE) sequence, a gradient echo (GRE) sequence, etc. Merely by way of example, a radial 3D UTE sequence may be provide to the MRI Scanner 110. In some embodiments, the pulse sequence may be sent to the MRI Scanner 110 in a form of a timing diagram. In some embodiments, the MR scan may be a pre-scan, within which a few steps, for example, quick shimming, coil tuning/matching, center frequency calibration, and transmitter gain adjustment, may be included. In some embodiments, the pre-scan may be performed to calibrate a gradient delay caused by the time delay when switching on/off the gradient magnetic field generator. In some embodiments, an MR signal may be acquired during the MR scan. In some embodiments, the acquired MR signal may be an analog signal.

In 206, the MR signal acquired during the MR scan may be processed by, for example, the processing module 130. Various signal processing methods may be applied to process the acquired signal. Merely by way of example, the signal processing methods may include analog-to-digital conversion, linear fitting, 2D Fourier transform (2D FT), fast Fourier transform (FFT), interpolation algorithm, regridding, or the like, or any combination thereof. In some embodiments, the acquired signal may be converted to a set of discrete data. Furthermore, the discrete data may be processed to fill into the k-space. Also, the filled k-space may be processed to calibrate the gradient delay in an imaging scan.

In 208, an MR image may be generated based on the processed signal. In some embodiments, the image may be generated by repeating 202 through 206 for a certain number of times. In some embodiments, the certain number of times may be determined by the MRI system 100 or provided by a user (e.g., a doctor). The generated image may be a $T_1$-weighted image, a $T_2$-weighted image, a PD (proton density)-weighted image, a FLAIR (fluid attenuated inversion recovery) image, or the like. In some embodiments, the image may be further processed to generate a report including the reconstructed image. The image and/or the generated report may be output to a related device (e.g., to be printed, to be displayed, or the like).

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, the process may further include an operation between 204 and 206 for storing the acquired MR signal.

Figure 3:
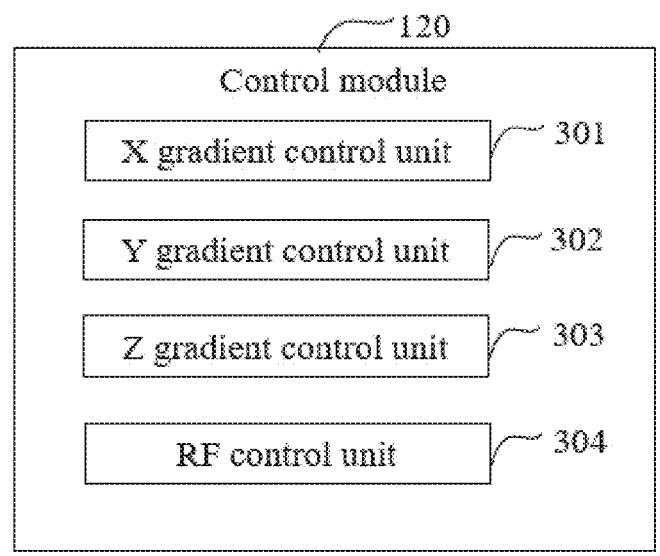
FIG. 3 is a block diagram illustrating the control module 120 according to some embodiments of the present disclosure.

FIG. 3 is a block diagram illustrating the control module 120 according to some embodiments of the present disclosure. The control module 120 may include an X gradient control unit 301, a Y gradient control unit 302, a Z gradient control unit 303, and an RF control unit 304.

The X gradient control unit 301, the Y gradient control unit 302, and the Z gradient control unit 303 may control the magnet module 111 to generate magnet field gradients in the X direction, the Y direction, and the Z direction, respectively. The X gradient control unit 301 may control the polarity, waveform, strength, and/or timing of the magnet field gradients in the X direction. The Y gradient control unit 302 may control the polarity, waveform, strength and/or timing of the magnet field gradient in the Y direction. The Z gradient control unit 303 may control the polarity, waveform, strength and/or timing of the magnet field gradients in the Z direction. In some embodiments, the magnet field gradients in the X direction, the Y direction, or the Z direction may include an encoding gradient and/or a readout gradient. As used herein, the encoding gradient may be used to spatially encoding signals from a part of an imaged subject (e.g., an organ, a tissue, etc.) from another; the readout gradient may be used to readout echo signals that may be used to generate an MR image. The X gradient control unit 301, the Y gradient control unit 302, or the Z gradient control unit 303 may be coupled with the magnet module 111, the processing module 130, and/or the display module. Merely by way of example, the X gradient control unit 301 may receive a command sent from the display module 140 provided by, e.g., a user. In some embodiments, the command may relate to the timing sequence of the readout gradient in the X direction. In some embodiments, the command may be sent to the magnet module 111.

The RF control unit 304 may control the RF module 112 to generate RF excitation pulses. In some embodiments, the RF control unit 304 may control the radio frequency, the phase, the amplitude and/or the waveform of the radio frequency pulse. In some embodiments, the RF control module 120 may be coupled with the RF module 112, the processing module 130, and/or the display module 140. Merely by way of example, the RF control unit 304 may send a command to the RF module 112 to control the radio frequency of the radio frequency pulse generated thereby.

It should be noted that the above description of the control module 120 is merely provided for the purposes of illustration, and not intended to limit the scope of the present disclosure. For persons having ordinary skills in the art, multiple variations and modifications may be made under the teachings of the present disclosure. For example, the assembly and/or function of the control module 120 may be varied or changed according to specific implementation scenarios. Merely by way of example, a magnet field gradient in an arbitrary direction may be generated by a specifically designed gradient control unit (e.g., similar with the X/Y/Z gradient control unit but in a different direction), or by a superposition of the magnet field gradients in the X, Y, and/or Z direction. However, those variations and modifications do not depart from the scope of the present disclosure.

Figure 4:
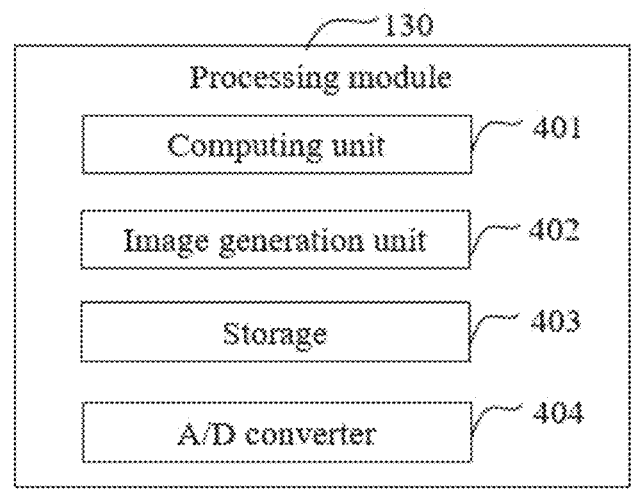
FIG. 4 is a block diagram illustrating the processing module 130 according to some embodiments of the present disclosure.

FIG. 4 is a block diagram illustrating the processing module 130 according to some embodiments of the present disclosure. Note that the construction of the processing module 130 may have some other variations, and that FIG. 4 is provided for illustration purposes. The processing module 130 illustrated in FIG. 1 may process information before, during, or after an MR scan. The processing module 130 may be a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an ARM, or the like, or any combination thereof. As shown in FIG. 4, the processing module 130 may include a computing unit 401, an image generation unit 402, a storage 403, and an A/D converter 404.

The computing unit 401 may determine different kinds of information generated from the MRI Scanner 110, or received from the control module 120 and/or display module 140. In some embodiments, the information from the MRI Scanner 110 may be a plurality of MR signals of an imaged subject. In some embodiments, the MR signals may include an echo wave, a half echo wave, or a signal between an echo wave and a half echo wave (also referred to as "partial echo signal"). In some embodiments, the computing unit 401 may determine a gradient delay value based on the MR signals. The gradient delay value may be a gradient delay value for the gradient magnetic field in the X direction, the Y direction, the Z direction, or any other directions in a coordinate system. In some embodiments, the gradient delay value may correspond to a k-space shift along a radial spoke in a 3D k-space coordinate. In some embodiments, the radial spoke may be determined by the condition of the MRI system 100. In some embodiments, the k-space shift along the radial spoke may be determined based on the gradient delay value for the X direction, the Y direction, and/or the Z direction. In some embodiments, the gradient delay value may be used to calibrate k-space data (also referred to as "k-space data line") generated by an imaging scan. In some embodiments, the gradient delay value may be generated by performing the pre-scan. In some embodiments, the pre-scan may be performed for calibrating the MRI system 100, while the imaging scan may be performed for generating a magnetic resonance (MR) image. The k-space data may be generated by filling an MR signal generated by an imaging scan into the k-space. For example, a first set of MR signals may be filled into the k-space along a specific trajectory, forming a first data line in the k-space.

In some embodiments, the information from the control module 120 may include information about the MRI Scanner 110, the magnet module 111, a patient position (e.g., within the MRI system 100), the RF module 112, or the like, or any combination thereof. In some embodiments, the information may be a patient position, the main and/or gradient magnet intensity, the radio frequency phase and/or amplitude, etc. The information from the display module 140 may include information from a user and/or other external resource. Exemplary information from a user may include parameters regarding image contrast and/or ratio, a subject of interest (e.g., the type of tissue to be imaged, etc.), slice thickness, an imaging type (e.g., T1 weighted imaging, T2 weighted imaging, proton density weighted imaging, etc.), T1, T2, a spin echo type (e.g., spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof.

The computing unit 401 may process the different kinds of information acquired from the MRI Scanner 110, control module 120 and/or display module 140. Various operations may be performed on t different kinds of information. Exemplary operations may include Fourier transform (FFT), regridding, interpolation algorithm, orthographic projection, matrix transformation, least square algorithm, linear fitting, recursion, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof. In some embodiment, the computing unit 410 may generate a set of k-space data points to fill the k-space based on the acquired echo signal utilizing the computing methods mentioned above. In some embodiment, the computing unit 410 may determine a gradient delay value representing the k-space shift utilizing one or more of the operations mentioned above.

The image generation unit 402 may connect to the computing unit 401, the MRI Scanner 110, the Magnet module 111, the display module 140, and/or the storage 403. In some embodiments, the image generation unit 402 may receive information from the MRI Scanner 110, the computing unit 401, and/or the storage 403. In some embodiments, the information may be an MR signal, or k-space data line relating to the MR signal. Merely by way of example, the image generation unit 402 may generate an MR image based on the calibrated k-space data line. The image generation unit 402 may employ different kinds of imaging reconstruction techniques for the image reconstruction procedure. Exemplary image reconstruction techniques may include Fourier reconstruction, constrained image reconstruction, regularized image reconstruction in parallel MRI, or the like, or any combination thereof.

The storage 403 may store the information that may be used by the computing unit 401 and/or the image generation unit 402. The information may include programs, software, algorithms, data, text, number, images and some other information. These examples are provided here for illustration purposes, and not intended to limit the scope of the present disclosure. Algorithms stored in the storage 403 may include recursion, a bisection method, a divide and conquer algorithm, a dynamic programming method, an iterative method, a branch-and-bound algorithm, a backtracking algorithm, or the like, or any combination thereof. In some embodiments, the storage 403 may store MR signals generated by the MRI scanner 110.

The A/D converter 404 may convert analog MR signals to digital MR signals. In some embodiments, one or more parameters may be set before or during the conversion, e.g., voltage, current, rate, sampling frequency, or the like, or a combination thereof. The converted MR signals may be stored in the storage 403.

It should be noted that the above description of the processing module 130 is merely provided for the purposes of illustration, and not intended to limit the scope of the present disclosure. For persons having ordinary skills in the art, multiple variations or modifications may be made under the teachings of the present disclosure. For example, the assembly and/or function of processing module 130 may be varied or changed. In some embodiments, the computing unit 401 and the image generation unit 402 may share one storage 403. While in some embodiments, the computing unit 401 and the image generation unit 402 may have their own storage blocks, respectively. However, those variations and modifications do not depart from the scope of the present disclosure.

Figure 5:
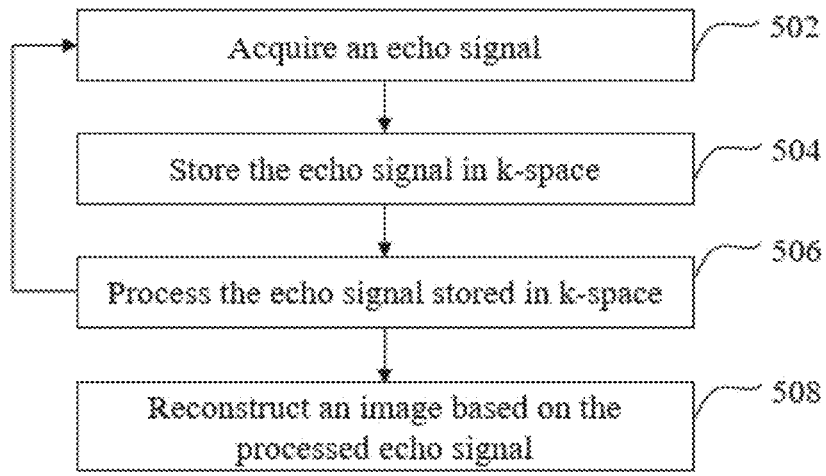
FIG. 5 is a flowchart illustrating the processing of an MR signal according to some embodiments of the present disclosure.
Figure 6A:
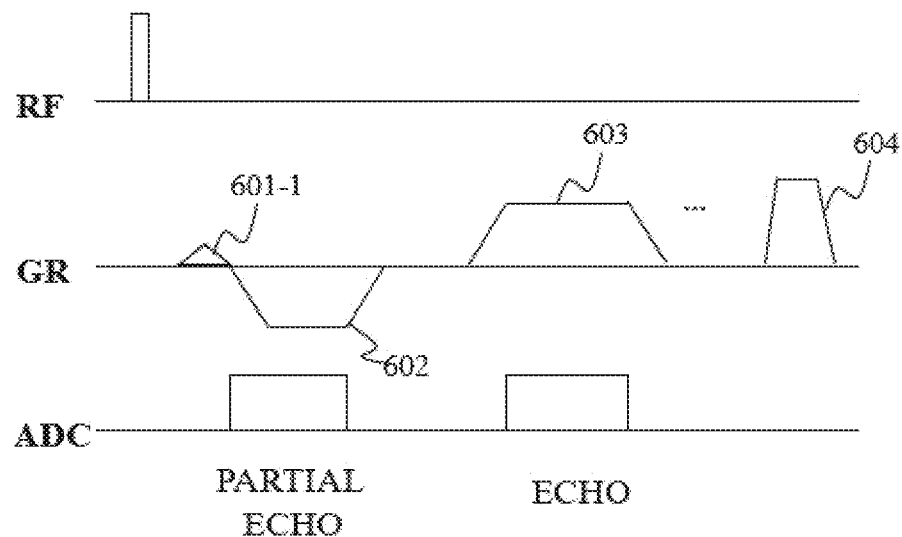
FIG. 6A illustrates an exemplary timing diagram of magnetic gradients for an MR scan according to some embodiments of the present disclosure.

FIG. 5 is a flowchart illustrating the processing of an MR signal according to some embodiments of the present disclosure. In 502, an echo signal may be acquired. The echo signal may be echo wave acquired by, for example, the MRI Scanner 110. In some embodiments, the acquired echo signal may be a spin echo (SE), 3D fast spin echo (3D FSE), gradient echo (GRE), fast double echo (FADE). In some embodiments, the acquired echo signal may be a free induction decay (FID) signal. The echo signal may be a half echo wave, a full echo wave, or a partial echo signal. In some embodiments, the echo signal may be an analog signal. The echo signal may be generated in an imaging scan or a pre-scan by, for example, applying a dephaser gradient as illustrated in FIG. 6A and/or FIG. 6B, and the description thereof. In some embodiments, the signal may be acquired by the MRI Scanner 110.

In 504, the acquired echo signal may be stored in the k-space. In some embodiments, the acquired echo signal may be processed before being stored into the k-space. Exemplary operations may include high-pass filtering, smoothing algorithm, analog to digital conversion, etc. Specifically, the operations may be performed by converting the analog echo signal into a digital signal by the AD convertor 404. In some embodiments, the acquired echo signal may be sampled according to a sampling algorithm to generate a set of discrete data to be filled into the k-space. There may be various sampling technique for the filling of the k-space with the acquired signal, including Cartesian sampling (row by row), radial sampling, spiral sampling, zig-zag sampling, etc. As used herein, the radial sampling may refer to a sampling technique in which an echo signal is filled along a radial spoke (also referred to as "a trajectory") to form a data line in the k-space. For a three-dimensional radial sampling, the k-space may have a shape of a sphere, and the k-space may be filled along radial spokes of the sphere. In some embodiments, the radial spokes may start from the center of the k-space, and end on a spherical surface in the k-space (also referred to as "center out trajectories"). Merely by way of example, under the radial sampling, the acquired echo signal may be filled along radial spokes in the k-space.

In 506, the echo signal stored in the k-space may be processed. Various operations may be utilized to process the echo signal stored in the k-space. For example, the various operations may include linear fitting, least squares operation, 2D Fourier transform (2D FT), Z-transform, Laplace transform, principle component analysis (PCA), nearest neighbor interpolation, regridding, iteration, or the like, or any combination thereof. In some embodiments, the echo signal stored in the k-space may be calibrated and transformed into an image domain. In some embodiments, the echo signal may be further processed with one or more operations exemplified above to eliminate errors or artifacts resulted from, for example, motion, interference, shadowing, incomplete data, k-space shift, k-space distortion, over sampling, under sampling, etc. In some embodiments, step 502 through step 506 may be repeated for obtaining adequate k-space data lines before the image reconstruction is performed.

In 508, an image may be reconstructed based on the processed echo signal. Exemplary image reconstruction techniques may include Fourier reconstruction, inverse Fourier transform, constrained image reconstruction, regularized image reconstruction in parallel MRI, or the like, or any combination thereof. In some embodiments, the reconstructed image may be further processed to generate a report regarding the reconstructed image. In some embodiments, one or more post processing operations may be applied to the reconstructed image. The post processing operations may relate to geometrical processing, arithmetic processing, image enhancement, image restoration, 3D image reconstruction, or the like, or any combination thereof. Merely by way of example, the post processing operations may include magnification, distortion correction, image sharpening, image softening, pseudo color processing, and/or wiener filtering. In some embodiments, the image may be compressed to a standard format for handling, printing, storing, or transmitting the MRI data, for example, digital imaging and communications in medicine (DICOM).

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, for reconstruction of non-Cartesian MRI data (e.g., data obtained from radial sampling), the process may return to 504 after signal processing, in which regridding may be applied and the echo signal may be stored in a Cartesian k-space.

Figure 6B:
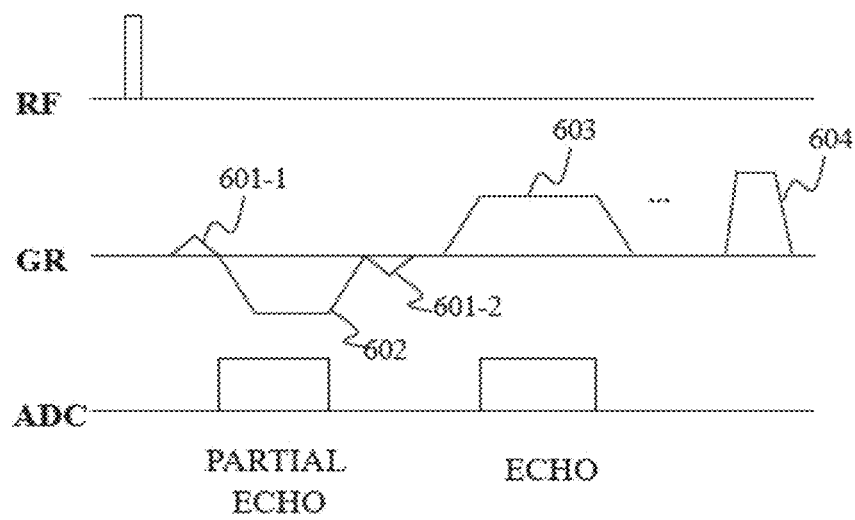
FIG. 6B illustrates another exemplary timing diagram of magnetic gradients for an MR scan according to some embodiments of the present disclosure.

FIG. 6A and FIG. 6B show two exemplary timing diagram of pulse sequences for an MR scan according to some embodiments of the present disclosure. In some embodiments, the MR scan may include a pre-san pulse configured to calibrate the MRI system 100. The timing diagram may indicate a series of radio-frequency (RF) excitation pulses and magnetic field gradient pulses (also referred to as "readout gradients") applied in the MR scan. An echo signal may be generated by applying the RF excitation pluses and the readout gradients in an MR scan. In some embodiments, a partial echo signal may be acquired. In some embodiments, a full echo signal may be acquired. The acquisition of the echo signal may be implemented by an analog-to-digital convertor (ADC), when the acquired echo signal is filled into k-space. As is illustrated in FIG. 6A and/or FIG. 6B, the readout gradients may include a dephasing gradient 602 (also referred to as "imaging pulse"), a rephasing gradient 603, and a spoiler 604. In some embodiments, a pre-scan may be performed by adding a dephaser gradient 601-1 (also referred to as "pre-scan pulse") and/or a dephaser gradient 601-2 in the readout gradients. As is illustrated in FIG. 6A, the dephaser gradient 601-1 may be applied between the radio-frequency (RF) excitation pulse and the ramp up of the dephasing gradient 602. The polarity of the dephaser gradient 601-1 may be opposite to the polarity of the dephasing gradient 602. As is illustrated in FIG. 6B, the dephaser gradient 601-2 may be applied between the dephasing gradient 602 and the ramp up of the rephrasing gradient 603. The polarity of the dephaser gradient 601-2 may be same with the polarity of the dephasing gradient 602. In some embodiments, the waveform of the dephaser gradient 601-1 and/or the dephaser gradient 601-2, the dephasing gradient 602, the rephrasing gradient 603, and/or the spoiler 604 may be uniform (e.g., rectangle, trapezoid, etc.) or non-uniform (e.g., asymmetric waveform). In some embodiments, the readout gradient may be applied in the X direction, in the Y direction, in the Z direction, or in any other direction through the gradient coils in different directions of the MRI system 100.

Figure 6C:
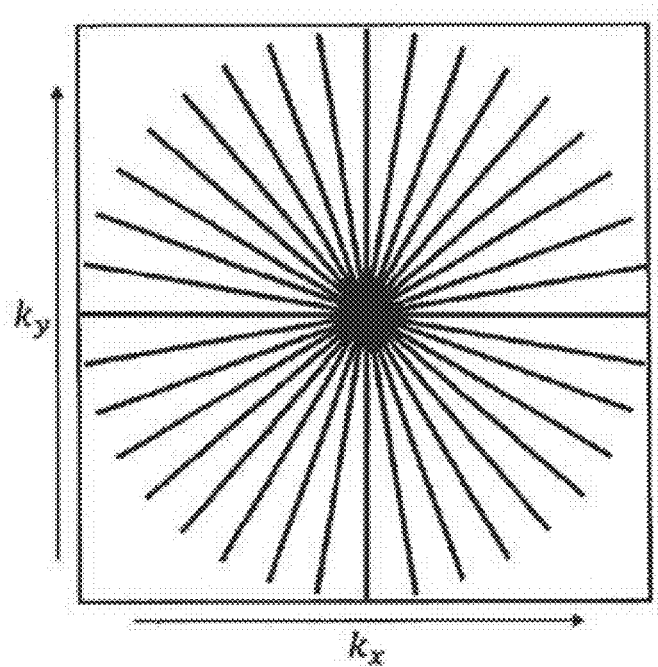
FIG. 6C shows an exemplary two-dimensional radial sampling of k-space according to some embodiments of the present disclosure.

FIG. 6C shows an exemplary two-dimensional radial sampling of k-space according to some embodiments of the present disclosure. For a two-dimensional radial sampling, the k-space that constituted by X direction in the k-space (i.e., $k_x$) and Y direction in the k-space (i.e., $k_y$) may have a round shape, and radial spokes in the k-space may start from the center of the k-space, and end on a round surface (also referred to as "center out trajectories"). The echo signal generated by applying a pulse sequence (for example, the pulse sequences as illustrated in FIG. 6A and/or FIG. 6B) may be filled into k-space to form a data line along a certain trajectory. In some embodiments, radial sampling may be applied on a partial echo signal acquired in the pre-scan. The acquired partial echo signal may be filled into k-space along a corresponding radial spoke (trajectory) to form a data line in the k-space. In some embodiments, the partial echo signal may be filled into the radial spoke passing through the k-space center, and ending on the round surface. Similarly, for a three-dimensional radial sampling, the k-space that constituted by X direction in the k-space (i.e., $k_x$), Y direction in the k-space (i.e., $k_y$) and Z direction in the k-space (i.e., $k_z$) may have a shape of sphere. The spatial sampling of the three-dimensional k-space may be similar to the two-dimensional radial sampling as described elsewhere in the disclosure.

Figure 7:
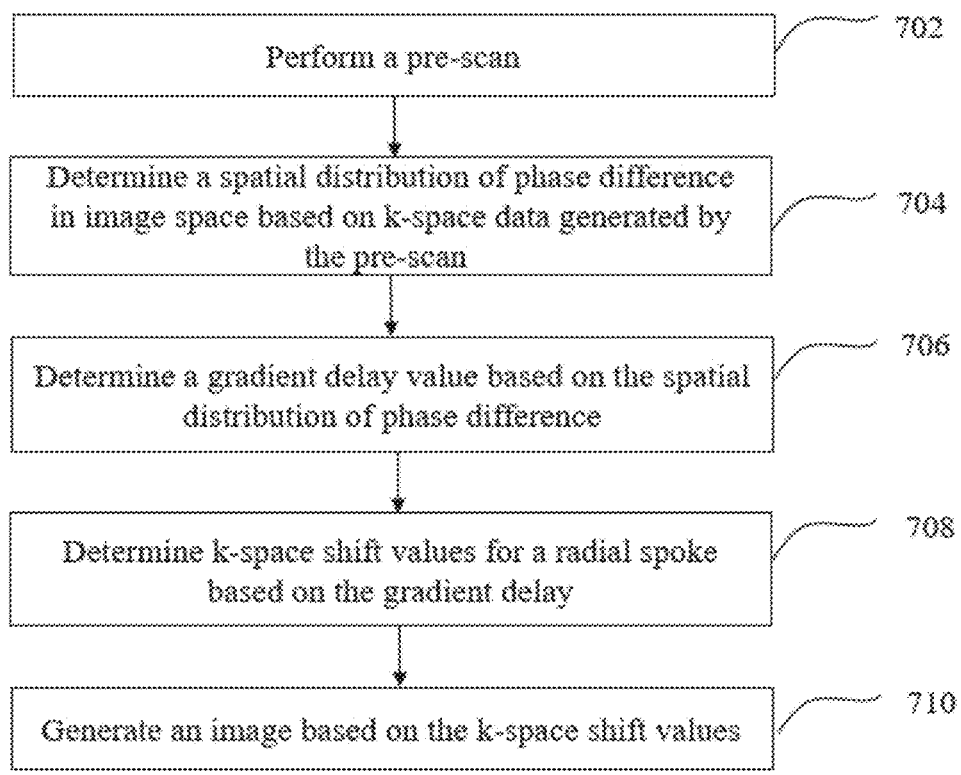
FIG. 7 is a flowchart illustrating a process for generating a calibrated MR image according to some embodiments of the present disclosure.

FIG. 7 is a flowchart illustrating a process for generating a calibrated MR image according to some embodiments of the present disclosure. In 702, a pre-scan may be performed. The pre-scan may be performed on a phantom or on a subject (e.g., a patient). As used herein, a phantom may refer to a specially designed subject that is scanned or imaged to evaluate the performance of the imaging devices. In some embodiments, the pre-scan may be performed for anatomical regions, for example, the brain of a subject, a lung of a subject, the heart of a subject, or the like, or a combination thereof. In some embodiments, the pre-scan may be performed for the same region as in an imaging scan.

The pre-scan may be performed by applying the dephaser gradient 601-1 in the readout gradient as illustrated in FIG. 6A and the description thereof. The dephaser gradient 601-1 may occur between the radio-frequency (RF) excitation pulse and the ramp up of the dephasing gradient 602. In some embodiments, a partial echo signal may be acquired during the pre-scan. In some embodiments, a plurality of partial echoes may be acquired by repetitions of the RF excitation pulses and the readout gradients including the dephaser gradient 601-1.

The acquired partial echo signals may be filled into the k-space. The k-space may be a two dimensional (2D) k-space or a three dimensional (3D) k-space. In some embodiments, multiple points may be selected from the partial echo signal to be filled, as k-space data points, into the k-space in the k-space sampling. Exemplary k-space sampling techniques may include Cartesian sampling, spiral sampling, radial sampling, zig-zag sampling, etc. In some embodiments, radial sampling may be applied in the pre-scan, the partial echo signal may be filled, as the k-space data points, into k-space along the radial spokes. The points in the partial echo signal corresponding to the k-space data line along a radial spoke may be generated by activating magnetic field gradients in a certain direction. The activation of the magnetic field gradients may be achieved by the X gradient control unit 301, Y gradient control unit 302, and/or Z gradient control unit 303.

In the pre-scan, k-space data lines along certain radial spokes may be acquired. In some embodiments, a first k-space data line along a first trajectory may be acquired, and a second k-space data line along a second trajectory, with a reverse direction relative to the first trajectory, may be acquired. For example, the first k-space data line may correspond to a first trajectory in the k-space with an angle of 0°, and the second k-space data line may correspond to a second trajectory in the k-space with an angle of 180°.

In 704, a spatial distribution of phase difference in the image domain corresponding to different radial spokes in the k-space may be determined. Firstly, the k-space data line along a radial spoke may be transformed into an image domain to generate a corresponding image signal. The transformation may be performed according to an algorithm including, for example, Fourier transform (FT), fast Fourier transform (FFT), non-uniform fast Fourier transform (NUFFT), or the like, or any combination thereof. In some embodiments, one or more other operations including regridding, interpolation, etc., may be performed in the transformation. By way of the transformation, a first image signal corresponding to the first k-space data line and a second image signal corresponding to the second k-space data line may be obtained. In some embodiments, the first image signal and/or the second image signal may be one-dimensional signal(s) whose amplitude may vary along a direction in the image domain corresponding to the first and second radial spokes in the k-space. As used herein, an image signal may include amplitude, frequency, and phase information of the k-space data points along the radial spoke. In some embodiments, the image signal may take a form of a phase curve along the radial spoke. The horizontal axis of the phase curve may represent k-space data points along a radial spoke, and the vertical axis may represent the phase value of the k-space data points.

In some embodiments, a first phase curve and a second phase curve in the image space may be determined. The first phase curve may correspond to the first k-space data line along the first radial spoke. The second phase curve may correspond to the second k-space data line along the opposite radial spoke. The phase difference between the first phase curve and the second phase curve may be determined. In some embodiments, the phase difference may be represented by a phase difference curve. In some embodiments, the slope of the phase difference curve may be determined. In some embodiments, the slope of the phase difference curve may represent the spatial distribution of phase difference for one dimensional image signal in image space. The slope may be a constant in some cases (i.e., the phase difference curve may be a straight line in certain regions).

In 706, a gradient delay value may be determined based on the spatial distribution of the phase difference. The gradient delay value may represent a delay in the time of the gradient magnetic field generated in the MR scan. In some embodiments, the gradient delay may lead to a shift of the k-space data line along a radial spoke in a certain direction. For example, the gradient delay may lead to a shift (the shift may be different for different data points on the line) of the k-space relative to the center of the k-space (also referred to as "k-space center"). A k-space shift value may be generated to calibrate the k-space shift by detecting the k-space center. In some embodiments, the k-space shift value may be determined based on the phase difference between the first phase curve and the second phase curve. In some embodiments, the k-space shift value may be determined based on the spatial distribution of the phase difference (e.g., the slope of the phase difference curve). In some embodiments, the k-space shift value may be determined based on the relationship between the image space and the k-space. The k-space shift value may be assessed based on the shift property of the Fourier transform. More description regarding the k-space shift value may be found in elsewhere in the present disclosure. See, for example, FIG. 8 and the description thereof. Based on the k-space shift value, the gradient delay value may be determined. In some embodiments, a coefficient may be provided as one of the factors for the determination of the gradient delay value. The coefficient may be set by an operator, determined based on the status of the MRI system 100, time efficiency, or the like, or a combination thereof.

In 708, k-space shift values for a radial spoke in the k-space may be determined based on the gradient delay value obtained in 706. In some embodiments, the gradient delay values in different directions in the coordinate system may be determined by carrying out 702 through 706 while performing pre-scans. The gradient delay values in different directions may be further transformed to the magnetic field gradient delay values for the X axis, the Y axis, and the Z axis of the coordinate system. In some embodiments, the gradient delay values in different directions may be converted into gradient delay values on the X axis, the Y axis, and the Z axis of the coordinate system by an orthographic projection operation. The X axis, the Y axis, and the Z axis may correspond to the positions of the X gradient coils, the Y gradient coils, and the Z gradient coils, a patient body, or the orientation of the bed, etc. Then, the k-space shift values for an arbitrary radial spoke in the k-space may be determined based on the magnetic field gradient delay values on the X axis, the Y axis, and the Z axis.

In 710, an imaging scan may be performed to generate an image based on the k-space shift values. In some embodiments, the k-space data line generated by the imaging scan may be calibrated based on the k-space shift values obtained in 708. The imaging scan may be an MRI scan for generating images. In some embodiments, the imaging scan may be a 3D radial UTE scan. The k-space data line along a radial spoke generated by the imaging scan may be calibrated based on the k-space shift values for the radial spoke.

An image may be reconstructed based on the calibrated k-space data line generated by the imaging scan. The reconstruction technique may include Fourier transform (FT), fast Fourier transform (FFT), non-uniform fast Fourier transform (NUFFT). The k-space data points along the calibrated k-space data line may be non-uniform due to ramp sampling. As used herein, the non-uniform k-space data points may refer to the data points obtained by k-space sampling technique other than Cartesian sampling, such as radial sampling. In some embodiments, the non-uniform k-space data points may be converted to uniform k-space data points before an image is generated by performing regridding or interpolation. In some embodiments, an image may be generated based on the non-uniform k-space data points by non-uniform fast Fourier transform (NUFFT). In some embodiments, apodization may be performed to correct for the effect of regridding kernel. The reconstructed image may be a $T_1$-weighted image, a $T_2$-weighted image, a PD-weighted image, a FLAIR image, etc.

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, magnetic field gradient delay values for three arbitrary directions in the coordinate system may be used to determine the gradient delay value on the X axis, the Y axis, and the Z axis. In some embodiments, one of the three arbitrary directions may point out of the plane constituted by the other two directions.

Figure 8:
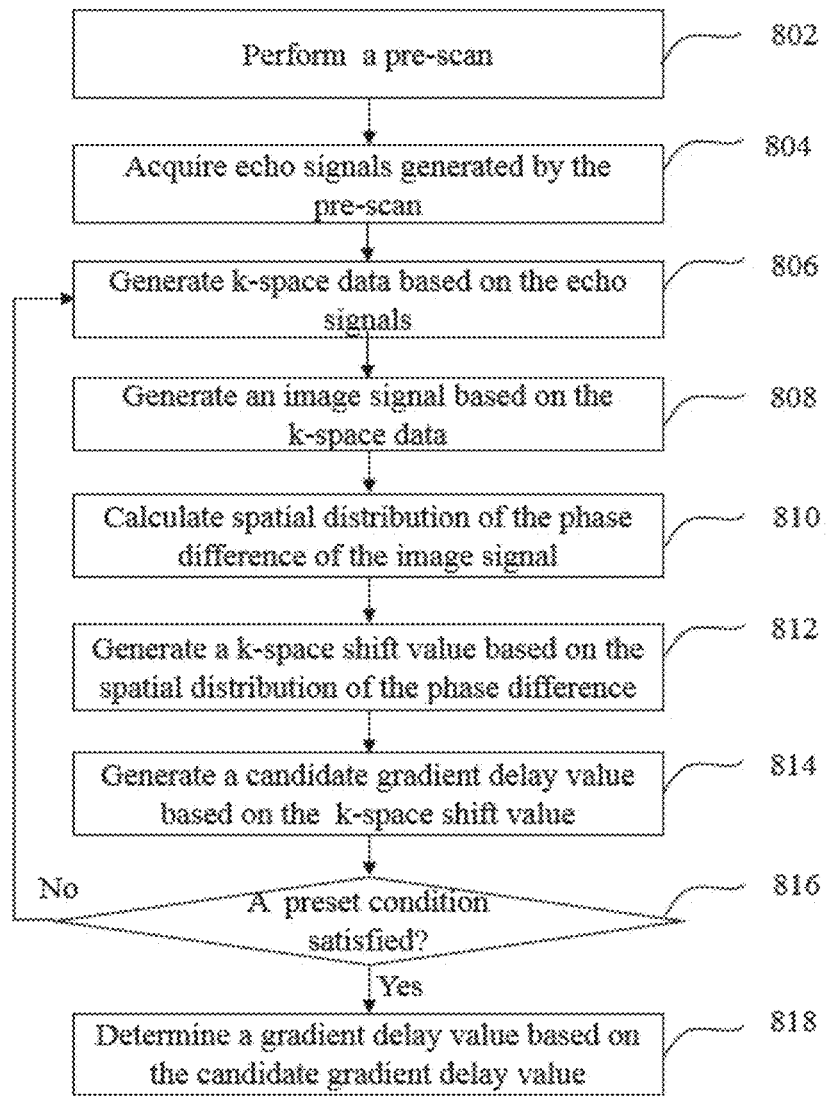
FIG. 8 is a flowchart of a process for determining a gradient delay value according to some embodiments of the present disclosure.

FIG. 8 is a flowchart of a process for determining the gradient delay value according to some embodiments of the present disclosure. In 802, a pre-scan may be performed. A parameter for the pre-scan may be set in the control module 120. In some embodiments, the parameter may include the gradient field, the sampling technique, the scanning direction, the pulse sequence, the echo time, etc. The pre-scan may include the dephaser gradient 601-1 in the readout gradient that may occur between the RF excitation pulse and the ramp up of the dephasing gradient, e.g., 602 as illustrated in FIG. 6A. In some embodiments, the dephaser gradient with a uniform gradient waveform (for example, triangle, trapezoid, rectangle) may be set for the pre-scan. In some embodiments, the dephaser gradient with a non-uniform gradient waveform (for example, with imperfections on an otherwise uniform gradient waveform), such as a slight fluctuation caused by the instability of the magnetic field, may be set for the pre-scan. In some embodiments, the imperfections of the gradient field may be calibrated based on the pre-scan. In some embodiments, one or more calibration technique may be utilized for the actual shape of the gradient field. See, for example, the k-space trajectory measurement technique as described in Jeff H. Duyn, *Simple Correction Method for k-Space Trajectory Deviations in MRI, JMR*, 150-153 (1998), which is hereby incorporated by reference.

The pre-scan may be performed prior to an imaging scan with a time interval between the pre-scan and the imaging scan. In some embodiments, the pre-scan may be performed prior to the imaging scan to determine a gradient delay value to calibrate the k-space shift. In some embodiments, the pre-scan may be performed before the imaging scan without a time interval.

In 804, an echo signal generated by the pre-scan may be acquired. In some embodiments, the generated signal may be the partial echo signal illustrated in FIG. 6A and/or FIG. 6B, and the description thereof. During the pre-scan, the echo signal may be generated by an RF excitation pulse and a gradient reversal. The gradient reversal may be implemented by the dephaser gradient in conjunction with the first gradient field in the readout gradient (e.g., dephasing gradient 602 in FIG. 6A and/or FIG. 6B). In some embodiments, the echo signal may be generated at the ramp up or the plateau of the readout gradient. In some embodiments, a plurality of echo signals may be generated by repetitions of the gradient reversal in the pre-scan.

In 806, a k-space data line may be generated based on the echo signal acquired in 804. The acquired echo signal may be filled into the k-space. In some embodiments, multiple points may be selected from the acquired echo signal to fill the k-space as k-space data points. The multiple points may be selected at a regular intervals or varying intervals. In some embodiments, the intervals may be determined by the gradient field as set in the pre-scan. In some embodiments, the multiple points may be filled into the k-space according to a k-space sampling technique. Exemplary k-space sampling techniques may include Cartesian sampling, spiral sampling, radial sampling, zig-zag sampling, etc.

For a three-dimensional radial sampling, the echo signal may be filled along a trajectory in the k-space that passes through the k-space center, and ends on a spherical surface in the k-space (also referred to as "boarder region"). In some embodiments, radial sampling may be applied in the pre-scan, and the acquired echo signal may be filled into k-space along a corresponding radial spoke.

The k-space data lines along radial spokes in different directions (including $k_x$, $k_y$, and $k_z$) may be acquired. In some embodiments, the k-space data lines along radial spokes in the positive direction and the negative direction along the X axis, the Y axis, or the Z axis in the k-space may be acquired. In some embodiments, a first k-space data line along a first trajectory in the k-space may be acquired, and a second k-space data line along a second trajectory in the opposite direction may be acquired subsequently. For example, the first trajectory and the second trajectory may be center-out trajectories, and the first trajectory may be opposite to the second trajectory. In some embodiments, the first k-space data line and the second k-space data line may be used to determine the gradient delay in a certain direction in a coordinate system in the image domain. For example, a first k-space data line along the positive direction of the X axis in the k-space and a second k-space data line along the negative direction of the X axis may be acquired to determine a gradient delay value.

In some embodiments, the k-space data line may be updated according to candidate gradient delay values. See description in connection with 814. The candidate gradient delay values may be generated by way of a plurality of iterations. In some embodiments, the iteration may stop when an eligible gradient delay value is obtained based on the candidate gradient delay values.

In 808, an image signal may be generated based on the k-space data line. The k-space data line may be converted into the image signal based on an algorithm. Exemplary algorithm may include Fourier transform (FT), fast Fourier transform (FT), discrete Fourier transform (DFT), or the like, or any combination thereof. In some embodiments, non-uniform k-space data points along the k-space data line may be subject to an intermediate processing to generate corresponding uniform k-space data points that are further converted into an image signal. Merely by way of example, the intermediate processing may include regridding, interpolation, etc. For example, non-uniform k-space data points may be converted into uniform k-space data points by piecewise constant interpolation, linear interpolation, polynomial interpolation, spline interpolation, multivariate interpolation, etc. As another example, non-uniform k-space data points may be converted into uniform k-space data points by Jacobian regridding, Voronoi regridding, Jackson regridding, Pipe regridding, etc. Then, the uniform k-space data points may be transformed into an image signal. In some embodiments, the transformation may be accomplished by FT, FFT, DFT, etc. In some embodiments, the non-uniform k-space data points may be transformed into an image signal directly by non-uniform Fourier transform (NUFFT).

In 810, a spatial distribution of phase difference in the image domain that corresponds to the radial spokes in the k-space may be generated. For illustration purposes, the radial spokes may be positioned along the $k_x$ in the following operations, which should not limit the scope of the present disclosure. A first k-space data line $S_+(k)$ along the positive direction of the X axis, and a second k-space data line $S_-(k)$ along the negative direction of the X axis may be acquired. In consideration of the k-space shift along the X axis due to gradient delay, the first k-space data line $S_+(k)$ may be expressed as $S(k-k_0)$, and the second k-space data line $S_-(k)$ may be expressed as $S(k+k_0)$. The corresponding image signal $I_+(x)$ in the image domain for the first signal $S_+(k)$ and $I_-(x)$ for the second signal $S_-(k)$ may be determined according to the following Equations (1) and (2), respectively:

$$I_+(x)=FT(S_+(x))=I(x)\exp^{(i\cdot k_0\cdot x)}. \quad (1)$$

$$I_-(x)=FT(S_-(x))=I(x)\exp^{(-i\cdot k_0\cdot x)}. \quad (2)$$

where FT may denote Fourier transform, and $k_0$ may denote the k-space shift due to the gradient delay. In some embodiments, the phase difference $\Delta\varphi$ in the image domain between the first image signal and second image signal may be determined. Through Equations (1) and (2), the spatial distribution of the phase difference $\delta_x$ between the first signal $I_+(x)$ and the second signal $I_-(x)$ (the phase difference along the X axis, e.g., the slope of the phase difference curve) may be determined according to the following Equation (3):

$$\delta_x = \frac{\Delta\varphi}{x}. \quad (3)$$

The phase difference $\Delta\varphi$ between signal $I_+(x)$ and $I_-(x)$ in the image domain may be determined based on Equation (4) in accordance with Equations (1) and (2):

$$\Delta\varphi=2k_0\cdot x. \quad (4)$$

Via Equations (3) and (4), the spatial distribution of the phase difference in the image domain (e.g., the slope of the phase difference curve) may be determined based on equation (5).

$$\delta_x=2k_0. \quad (5)$$

Therefore, the phase difference curve is linear along the X axis; in another word, the slope of the curve is proportional to the k-space shift $k_0$. The slope $\delta_x$ may be obtained by, for example, simple linear regression, least squares, or the like.

In 812, a k-space shift value along the X axis may be determined based on the spatial distribution of the phase difference in the image domain. A k-space shift value $\Delta k_x'$ along the X axis may be generated based on the slope $\delta_x$. The k-space shift value may be obtained according to the relationship between the image domain and the k-space. The k-space shift value may be determined by the shifting property of the Fourier transform. In some embodiments, the k-space shift value $\Delta k_x'$ may be determined according to Equation (6):

$$\Delta k_x' = \frac{\delta_x}{2\pi}\cdot m. \quad (6)$$

where m may denote the number of the multiple readout points on the radial spoke along the X axis.

In 814, a candidate gradient delay value may be generated based on the k-space shift value. The candidate gradient delay value $\Delta t$ may be the gradient delay value for gradient magnetic field in a certain direction in the coordinate system in the image domain. In some embodiments, the candidate gradient delay value $\Delta t$ may be determined by providing a predetermined coefficient. In some embodiments, the candidate gradient delay value $\Delta t$ may be determined by Equation (7):

$$\Delta t=C\cdot\Delta k_x'. \quad (7)$$

where C may be defined as the predetermined coefficient. The coefficient C may be set by an operator, or by the MRI system 100. In some embodiments, the coefficient C may be determined based on the status of the system, time efficiency, convergence of the iteration, or the like. For example, a larger coefficient may be used to speed up the convergence of the iteration. In some embodiments, the coefficient C may be constant or variable. For example, the coefficient C may be a constant during each iteration, such as 1, 0.5, 1.5, etc. In some embodiments, the coefficient C may be smaller than 2. As another example, the coefficient may vary, having a value of 2 in the first iteration, while a value of 1 in the second iteration.

In 816, a determination may be made as to whether a preset condition is satisfied. If the preset condition is satisfied, the process may proceed to 818. If the preset condition is not satisfied, the process may turn into another iteration within which operations 806 through 814 may be repeated to generate a new set of k-space data lines, and another candidate gradient delay value $\Delta t$ may be generated accordingly based on the new set of k-space data lines.

In some embodiments, the preset condition may include a maximum number of iterations (for example, 10 times) that when the maximum number of iterations is performed, the iteration may be stopped. The maximum number may be set by an operator, according to a default setting of the MRI system 100, etc. In some embodiments, the preset condition may be a threshold for the k-space shift value that when an eligible k-space shift value is obtained, the iteration may be stopped. The threshold for k-space shift value may be set by an operator, according to a default setting of the MRI system 100, etc. For example, the iteration may be ended when the k-space shift value obtained in the last iteration is smaller than a threshold. In some embodiments, the preset condition may be that the difference between a plurality of (e.g., two or more) k-space shift values or a plurality of (e.g., two or more) gradient delay values obtained in a plurality of (e.g., two or more) successive iterations is smaller than a threshold. When the preset condition is satisfied, the process may proceed to 818.

In 818, the MRI system 100 may generate a gradient delay value based on the candidate gradient delay value. The candidate gradient value $\Delta t$ determined in 814 from the latest iteration may be provided as the gradient delay value $\Delta T$. The gradient delay value $\Delta T$ may correspond to the gradient delay in a certain direction in the I coordinate system.

In some embodiments, a local search algorithm may be performed after the gradient delay value ΔT is determined in the preceding operations. The local search algorithm may sample a plurality of gradient delay values $\Delta T_i$ (i=1, 2, 3, 4, ..., n) based on the gradient delay value ΔT. In some embodiments, the sampled $\Delta T_i$ may be located within a predetermined range relative to ΔT, for example, ΔT±2 μsec. In some embodiments, the $\Delta T_i$ may be sampled at an interval within the sampling range, for example, at an interval of 0.1 μsec. The sampled $\Delta T_i$ (i=1, 2, 3, 4, ..., n) may be used to determine the value of a parameter. In some embodiments, the parameter may be a magnitude difference between two image signals that correspond to two radial spokes in reverse directions in the k-space. In some embodiments, one or more gradient delay values among $\Delta T_i$ (i=1, 2, 3, 4, ..., n) may be selected according to the determined parameter. In some embodiments, the selected one or more gradient delay values $\Delta T_i$ may correspond to a maximum value, a minimum value, a median value, or other characteristics of the parameter. In some embodiments, the selected gradient delay values $\Delta T_i$ may correspond to a minimum value of a magnitude difference in the image domain between first k-space data line along a first radial spoke and second k-space data line along a second radial spoke which is along the opposite direction relative to the first radial spoke. The selected one or more gradient delay values $\Delta T_i$ may replace the gradient delay value ΔT.

It should be noted that the above description is provided for the purposes of illustration, not intended to limit the scope of the present disclosure. For persons having ordinary skills in the art, multiple variations and modifications may be achieved in the light of the present disclosure. However, those variations and modifications do not depart from the scope of the present disclosure.

For example, the gradient delay value may be determined by k-space data line along radial spokes in any direction of the k-space during the pre-scan. As another example, the gradient delay value determined in the process may be magnetic field gradient delay for X, Y or Z axis, or any other directions in the coordinate system. As another example, the determination on whether the preset condition is satisfied may be performed after 810, within which the spatial distribution of the phase difference may be determined. Accordingly, the preset condition may include the slope of the phase difference curve being below a threshold. a maximum number of iterations to be performed (for example, 20 times), or the like.

Figure 9:
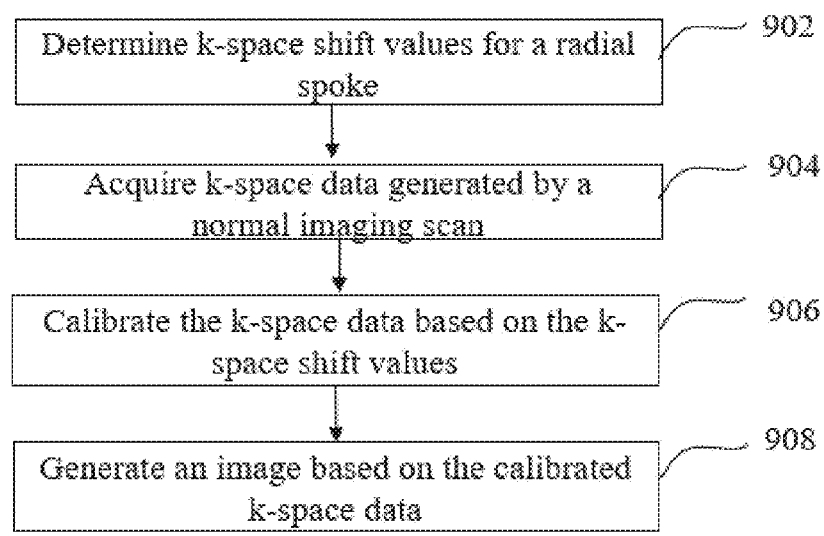
FIG. 9 is a flowchart of a process for generating an image based on the gradient delay value according to some embodiments of the present disclosure.

FIG. 9 is a flowchart of a process for generating an image based on the gradient delay value according to some embodiments of the present disclosure. In 902, k-space shift values for a radial spoke in the k-space may be determined based on the pre-scan. In some embodiments, the k-space shift values for data points along a radial spoke may be different. In some embodiments, the k-space shift values for radial spokes in different directions in the k-space may be different. In some embodiments, k-space shift values for all radial spokes across the k-space may be determined before an MR image is generated.

In some embodiments, the k-space shift values for all radial spokes in the k-space may be determined by repeating 802 through 812 as described in FIG. 8. In some embodiments, the k-space shift values for all radial spokes in the k-space may be determined based on the gradient delay values in certain directions in the coordinate system. The determination of the gradient delay values in certain directions in the coordinate system may be described elsewhere in the present application, for example, FIG. 8 and the description thereof. In some embodiments, at least three directions in the coordinate system may be selected and the gradient delay values for the three directions ΔT1, ΔT2, ΔT3 may be determined according to 802 through 818, respectively. It should be noted that the three directions may include a direction being oriented out of the plane constituted by the other two directions. In some embodiments, ΔT1, ΔT2, ΔT3 may be gradient delay values for the X axis, the Y axis, and the Z axis of the coordinate system. In some embodiments, an orthographic projection operation may be carried out to determine the gradient delay values for the X axis, the Y axis, and the Z axis when ΔT1, ΔT2, ΔT3 are not the gradient delay values for the X axis, the Y axis, and the Z axis. The gradient delay values for the X axis, the Y axis, and the Z axis may be different from each other. In some embodiments, the difference may relate to the condition of the MRI system 100 including, for example, the gradient coils, signal channels, or the like.

Referring back to the k-space, k-space shift values for all radial spokes may be determined based on the gradient delay values for the X axis, the Y axis, and the Z axis of the coordinate system. In some embodiments, a rotation matrix may be used for the transformation between the gradient delay values for the X axis, the Y axis, and the Z axis and the k-space shift values.

In 904, a k-space data line may be acquired in an imaging scan. The imaging scan may be an MRI scan for generating an image. In some embodiments, the imaging scan may be a 3D radial UTE scan. The imaging scan may be implemented by an RF pulse in conjunction with a gradient reversal (e.g., the dephasing gradient 602 and the rephrasing gradient 603). In some embodiments, a plurality of gradient reversal including multiple dephasing gradients and rephrasing gradients may be applied to generate multiple echo signals to fill the k-space. The dephasing gradient and the rephrasing gradient may be produced by a set of coils mounted within the MR scanner 110.

In some embodiments, radial sampling may be performed in the imaging scan. For a three-dimensional radial sampling, the acquired k-space data in the imaging scan may be filled into the k-space along a radial spoke starting from the k-space center, and ending on a spherical surface in the k-space. The sampling may continue to another radial spoke after the filling of the current radial spoke is finished, until adequate k-space data lines are sampled to generate an image.

In 906, the acquired k-space data line may be calibrated based on the k-space shift values determined in 902. In some embodiments, k-space shift values for all radial spokes may be determined before, during, or after the imaging scan. In some embodiments, the k-space shift value may correspond to the shift of the k-space data line on a radial spoke of the imaging scan. For example, the k-space shift value $\Delta k_r'$ may be used to calibrate the starting point shift of a radial spoke from (0, 0, 0) to $(k_x, k_y, k_z)$ in the k-space coordinate. Accordingly, the positions of each k-space data point on the radial spoke may be corrected based on the k-space shift values.

In 908, an image may be generated based on the calibrated k-space data line. An image may be reconstructed based on the calibrated k-space data line generated by the imaging scan. The reconstruction methods to generate the image may include Fourier transform (FT), fast Fourier transform (FFT), non-uniform fast Fourier transform (NUFFT), etc. In some embodiments, non-uniform k-space data points may be converted into image signal by way of an intermediate processing. In some embodiments, non-uniform k-space data points may be subject to an intermediate processing to generate corresponding uniform k-space data points. Merely by way of example, the intermediate processing may include regridding, interpolation, etc. For example, non-uniform k-space data points may be converted into uniform k-space data points by piecewise constant interpolation, linear interpolation, polynomial interpolation, spline interpolation, multivariate interpolation, etc. As another example, non-uniform k-space data points may be converted into uniform k-space data points by Jacobian regridding, Voronoi regridding, Jackson regridding, Pipe regridding, etc. Then, the uniform k-space data points may be transformed into an image signal. In some embodiments, the transformation may be accomplished by FT, FFT, DFT, etc. In some embodiments, the non-uniform k-space data points may be transformed into an image signal directly by non-uniform Fourier transform (NUFFT). In some embodiments, apodization may be performed to correct for the effect of regridding kernel. In some embodiments, image signals for reconstructing different images may be collected to generate a combined image. In some embodiments, the image signals for each image may originate from one of a plurality of gradient coils for receiving signals from different areas of an imaged object.

In some embodiments, one or more post processing techniques may be applied to the reconstructed image. The post processing techniques may relate to geometrical processing, arithmetic processing, image enhancement, image restoration, 3D image reconstruction, or the like, or a combination thereof. Merely by ways of example, the post processing techniques may include image magnification, distortion correction, image sharpening, image softening, pseudo color processing, wiener filtering, etc. In some embodiments, the image may be compressed to a standard format for handling, printing, storing, or transmitting MRI data, for example, digital imaging and communications in medicine (DICOM). In some embodiments, the reconstructed image may be further processed and a report regarding the reconstructed image may be generated. In some embodiments, the reconstructed image and/or the generated report may be output to a related device (e.g., to be printed, to be displayed, or the like). In some embodiments, the image may be generated by the imaging scan by repeating 902 through 906 until the gradient delay values on desired spokes in the k-space are obtained and an image is generated based on the k-space data lines corrected based on the gradient delay values.

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, the order of the steps in the process may be modified that 904 is processed prior to 902, i.e., the sampling of k-space data lines along a radial spoke in the imaging scan may be carried out before the k-space shift value for the radial spoke is determined.

Figure 10A:
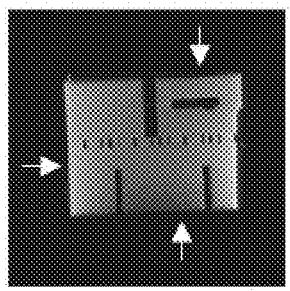
FIG. 10A through FIG. 10C illustrate three MR images reconstructed, by employing a uniform gradient waveform, without gradient delay correction according to some embodiments of the present disclosure.
Figure 10B:
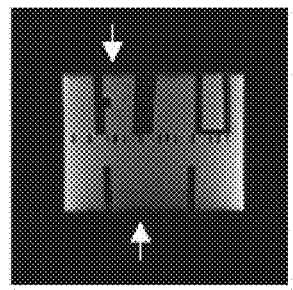
Figure 10C:
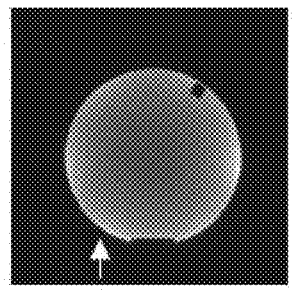
Figure 10D:
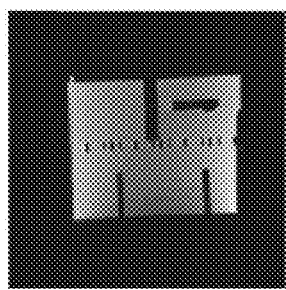
FIG. 10D through FIG. 10F illustrate three MR images reconstructed, by employing a uniform gradient waveform, with gradient delay being corrected according to some embodiments of the present disclosure.
Figure 10E:
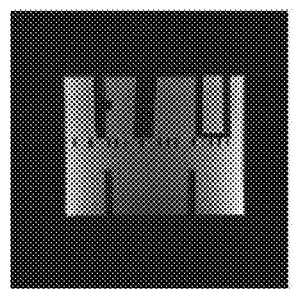
Figure 10F:
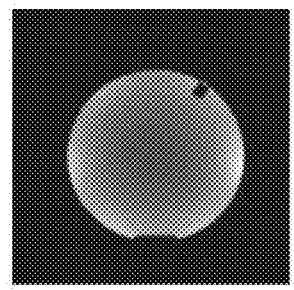
Figure 10G:
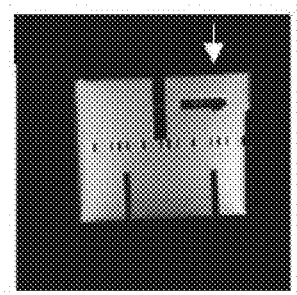
FIG. 10G through FIG. 10I illustrate three MR images reconstructed, by employing a non-uniform gradient waveform, without gradient delay correction according to some embodiments of the present disclosure.
Figure 10H:
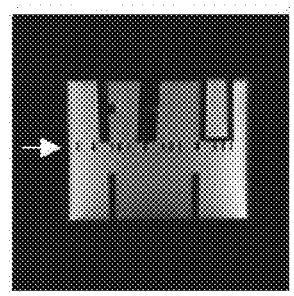
Figure 10I:
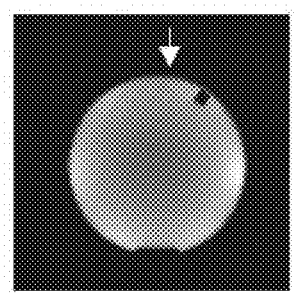
Figure 10J:
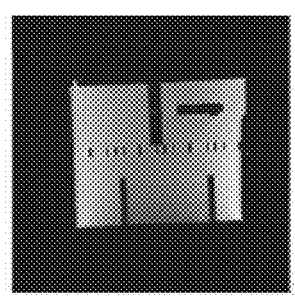
FIG. 10J through FIG. 10L illustrate three MR images reconstructed by employing a nonrectangular gradient waveform, with the gradient delay being corrected, according to some embodiments of the present disclosure.
Figure 10K:
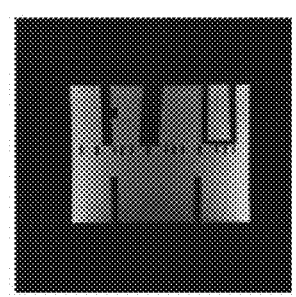
Figure 10L:
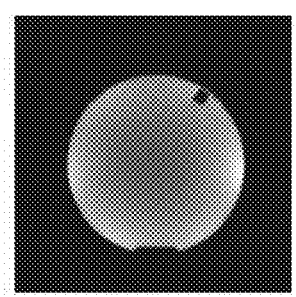

FIG. 10A through FIG. 10C illustrate three MR images reconstructed, by employing a uniform gradient waveform, without gradient delay correction according to some embodiments of the present disclosure. The arrows in the images in FIG. 10A through 10C point to artifacts in the images of a phantom that may relate to the gradient delay. FIG. 10D through FIG. 10F illustrate three MR images reconstructed, by employing a uniform gradient waveform, with gradient delay being corrected according to some embodiments of the present disclosure. No noticeable artifacts were observed in the images. FIG. 10G through FIG. 10I illustrate three MR images reconstructed, by employing a non-uniform gradient waveform, without gradient delay correction according to some embodiments of the present disclosure. The arrows in the images in FIG. 10G through 10I point to artifacts in the images of a phantom, which may relate to the gradient delay. FIG. 10J through FIG. 10L illustrate three MR images reconstructed by employing a nonrectangular gradient waveform, with the gradient delay being corrected, according to some embodiments of the present disclosure. No noticeable artifacts were observed in the images. The correction of the non-uniform gradient waveform are described elsewhere in the present disclosure. See, for example, FIG. 8 and the description thereof.

Figure 11A:
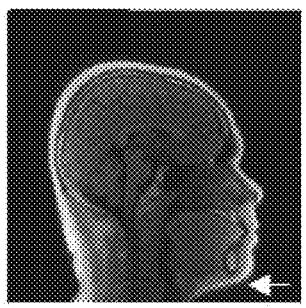
FIG. 11A through FIG. 11C illustrate three MR images reconstructed, by employing a uniform gradient waveform, without gradient delay correction according to some embodiments of the present disclosure.
Figure 11B:
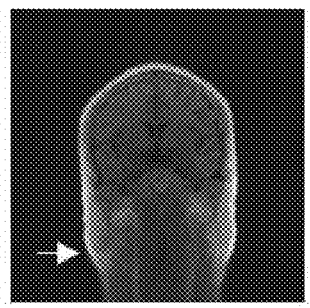
Figure 11C:
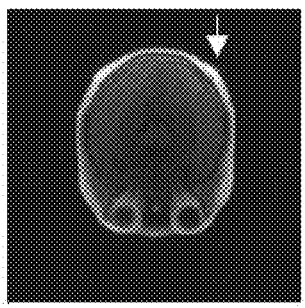
Figure 11D:
FIG. 11D through FIG. 11F illustrate three MR images reconstructed, by employing a uniform gradient waveform, with the gradient delay being corrected according to some embodiments of the present disclosure.
Figure 11E:
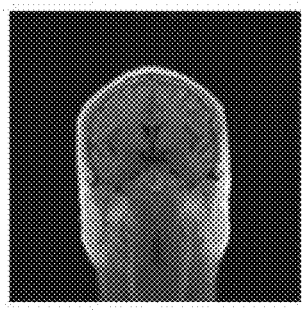
Figure 11F:
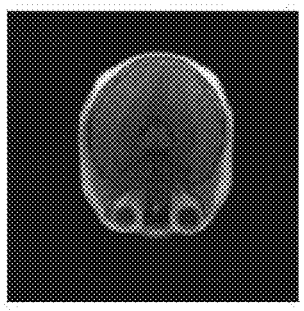
Figure 11G:
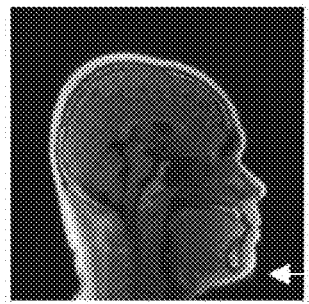
FIG. 11G through FIG. 11I illustrate three MR images reconstructed, by employing a non-uniform gradient waveform, without gradient delay correction, according to some embodiments of the present disclosure.
Figure 11H:
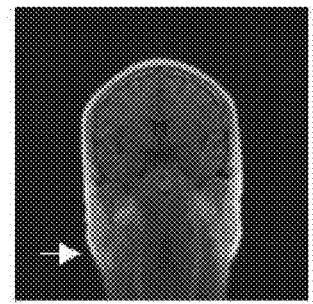
Figure 11I:
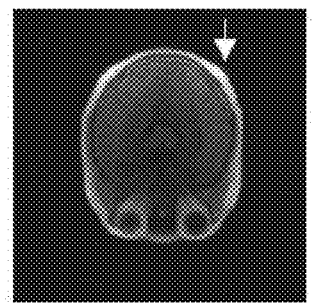
Figure 11J:
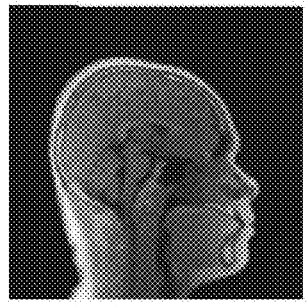
FIG. 11J through FIG. 11L illustrate three MR images reconstructed by employing a non-uniform gradient waveform, with the gradient delay being corrected, according to some embodiments of the present disclosure.
Figure 11K:
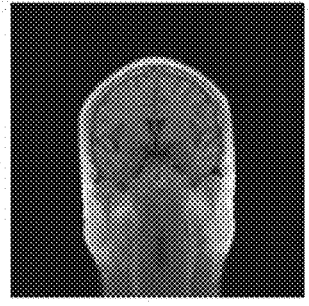
Figure 11L:
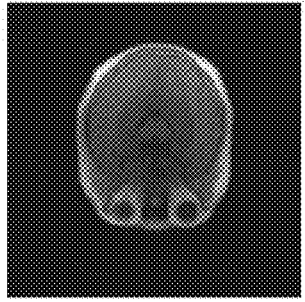

FIG. 11A through FIG. 11C illustrate three MR images reconstructed, by employing a uniform gradient waveform, without gradient delay correction according to some embodiments of the present disclosure. The arrows in the images in FIGS. 11A through 11C point to artifacts that may relate to the gradient delay. FIG. 11D through FIG. 11F illustrate three MR images reconstructed, by employing a uniform gradient waveform, with the gradient delay being corrected according to some embodiments of the present disclosure. No noticeable artifacts were observed in the images. FIG. 11G through FIG. 11I illustrate three MR images reconstructed, by employing a non-uniform gradient waveform, without gradient delay correction, according to some embodiments of the present disclosure. The arrows in the images in FIGS. 11G through 11I point to artifacts that may relate to the gradient delay. FIG. 11J through FIG. 11L illustrate three MR images reconstructed by employing a non-uniform gradient waveform, with the gradient delay being corrected, according to some embodiments of the present disclosure. No noticeable artifacts were observed in the images. The correction of the non-uniform gradient waveform are described elsewhere in the present disclosure. See, for example, FIG. 8 and the description thereof.

It should be noted that the above description is merely provided for the purposes of illustration, and not intended to limit the scope of the present disclosure. The image producing procedures in the present disclosure may be effective in reducing, removing or eliminating other types of motion artifacts including, for example, the vascular pulsation, heart movement, and random motion of the subject being scanned, or the like, or any combination thereof. The image producing procedures in the present disclosure may be applied to whole body MR imaging, and the images produced may have more clear structural details.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method for magnetic resonance imaging, comprising:
   acquiring a first set of MR signals and a second set of MR signals by applying a pulse sequence on a subject, the pulse sequence comprising at least an imaging pulse and a pre-scan pulse;
   obtaining a first data line by filling the first set of MR signals into k-space along a first trajectory;

obtaining a second data line by filling the second set of MR signals into k-space along a second trajectory;

determining a candidate k-space shift based on the first data line and the second data line, comprising
determining a phase difference in image domain based on the first data line and the second data line;
determining the candidate k-space shift based on the phase difference;

performing a plurality of iterations, each of the iteration comprising:
determining a candidate gradient delay based on the candidate k-space shift obtained from a prior iteration;
updating the first data line and the second data line based on the candidate gradient delay; and
updating the candidate k-space shift based on the updated first data line and the updated second data line;

determining the candidate gradient delay obtained in the last iteration as the gradient delay; and
reconstructing an image of the subject based on the gradient delay.

2. The method of claim 1, further comprising obtaining a calibrated data line by calibrating the first data line or the second data line based on the gradient delay, wherein the reconstructing an image of the subject is based on the calibrated data line.

3. The method of claim 1, wherein the first trajectory and the second trajectory pass through the k-space center, and the first trajectory is opposite to the second trajectory.

4. The method of claim 1, wherein the imaging pulse includes a UTE gradient, and the pre-scan pulse includes a dephaser gradient.

5. The method of claim 1, further comprising performing a regridding operation on the first data line or the second data line.

6. The method of claim 1, wherein the determining the candidate k-space shift based on the phase difference comprises:
determining a slope value according to the phase difference; and
determining the candidate k-space shift based on the slope value.

7. The method of claim 1, wherein the iteration is terminated when the slope value obtained in the last iteration is below a threshold.

8. The method of claim 1, wherein the gradient delay is in a first direction corresponding to the first trajectory and the second trajectory.

9. The method of claim 8, wherein the first direction is X direction, Y direction or Z direction.

10. The method of claim 8, further comprising
determining a second gradient delay in a second direction;
determining a third gradient delay in a third direction, the third direction is out of the plane defined by the first direction and the second direction;
acquiring a third set of MR signals by applying a pulse sequence on a subject;
obtaining a third data line by filling the third set of MR signals into k-space along a third trajectory;
determining a k-space shift along the third trajectory based on the first gradient delay, the second gradient delay and the third gradient delay; and
calibrating the third data line based on the third k-space shift along the third trajectory.

11. The method of claim 10, wherein the first direction is different from the second direction or the third direction.

12. A magnetic resonance system, comprising:
an MRI scanner configured to acquire a first set of MR signals and a second set of MR signals by applying a pulse sequence on a subject, the pulse sequence comprising at least an imaging pulse and a pre-scan pulse; and
a processing module configured to:
obtain a first data line by filling the first set of MR signals into k-space along a first trajectory;
obtain a second data line by filling the second set of MR signals into k-space along a second trajectory;
determine a candidate k-space shift based on the first data line and the second data line, comprising:
determine a phase difference in image domain based on the first data line and the second data line;
determine the candidate k-space shift based on the phase difference;
perform a plurality of iterations, each of the iteration comprising:
determine a candidate gradient delay based on the candidate k-space shift obtained from a prior iteration;
update the first data line and the second data line based on the candidate gradient delay; and
update the candidate k-space shift based on the updated first data line and the updated second data line;
determine the candidate gradient delay obtained in the last iteration as the gradient delay; and
reconstruct an image of the subject based on the gradient delay.

13. The system of claim 12, further comprising the processing module is configured to obtain a calibrated data line by calibrating the first data line or the second data line based on the gradient delay, wherein the reconstructing an image of the subject is based on the calibrated data line.

14. The system of claim 12, wherein the first trajectory and the second trajectory pass through the k-space center, and the first trajectory is opposite to the second trajectory.

15. The system of claim 12, wherein the imaging pulse includes a UTE gradient, and the pre-scan pulse includes a dephaser gradient.

16. The system of claim 12, further comprising the processing module configured to perform a regridding operation on the first data line or the second data line.

17. The system of claim 12, wherein the processing module is configured to determine the candidate k-space shift based on the phase difference by:
determining a slope value according to the phase difference; and
determining the candidate k-space shift based on the slope value.

18. The system of claim 12, wherein the number of iterations is less than 20.

19. A method for determining a gradient delay in a magnetic resonance system, comprising:
acquiring a first set of MR signals and a second set of MR signals by applying a pulse sequence on a subject, the pulse sequence comprising at least an imaging pulse and a pre-scan pulse;
obtaining a first data line by filling the first set of MR signals into k-space along a first trajectory;
obtaining a second data line by filling the second set of MR signals into k-space along a second trajectory;
determining a candidate k-space shift based on the first data line and the second data line, comprising:
determining a phase difference in image domain based on the first data line and the second data line;

determining the candidate k-space shift based on the phase difference;

iteratively determining the gradient delay based on a k-space shift in response to the first data line and the second data line determined based on the iterative process including iteratively updating the first data line and the second data line after each iteration of the iterative process based on an updated gradient delay determined by the most recent iteration of the iterative process.

20. The method of claim 19, wherein the determining the candidate k-space shift comprising:

determining a slope value according to the phase difference; and determining the candidate k-space shift based on the slope value.

* * * * *